(12) United States Patent
Wang et al.

(10) Patent No.: US 6,919,321 B2
(45) Date of Patent: Jul. 19, 2005

(54) OPHTHALMIC LUBRICATING SOLUTION ADAPTED FOR USE IN LASIK SURGERY

(75) Inventors: Pao-Li Wang, Fort Worth, TX (US); Uday Doshi, Randolph, NJ (US); Masoud R. Jafari, Arlington, TX (US); Kerry L. Markwardt, Mansfield, TX (US); Emerson Maddox, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/432,274

(22) PCT Filed: Nov. 29, 2001

(86) PCT No.: PCT/US01/44533
§ 371 (c)(1),
(2), (4) Date: May 19, 2003

(87) PCT Pub. No.: WO02/49611
PCT Pub. Date: Jun. 27, 2002

(65) Prior Publication Data
US 2004/0009893 A1 Jan. 15, 2004

Related U.S. Application Data

(60) Provisional application No. 60/257,304, filed on Dec. 20, 2000.

(51) Int. Cl.$^7$ ................... A61K 31/737; A61K 38/39; A61K 31/716; A61K 31/736; A61K 31/728
(52) U.S. Cl. .................. 514/54; 514/2; 514/8; 514/55; 514/57
(58) Field of Search ................. 514/2, 8, 54, 55, 514/57, 21

(56) References Cited

U.S. PATENT DOCUMENTS

| | | | |
|---|---|---|---|
| 4,255,415 A | | 3/1981 | Chrai et al. |
| 4,271,143 A | | 6/1981 | Schoenwald et al. |
| 4,550,022 A | | 10/1985 | Garabedian et al. |
| 4,851,513 A | * | 7/1989 | Devore et al. .............. 530/356 |
| 4,861,760 A | | 8/1989 | Mazuel et al. |
| 4,983,580 A | * | 1/1991 | Gibson .......................... 514/2 |
| 5,106,615 A | * | 4/1992 | Dikstein .................. 424/78.04 |
| 5,133,708 A | | 7/1992 | Smith |
| 5,277,911 A | | 1/1994 | Viegas et al. |
| 5,318,780 A | | 6/1994 | Viegas et al. |
| 5,409,904 A | | 4/1995 | Hecht et al. |
| 5,578,578 A | | 11/1996 | Hecht et al. |
| 5,587,175 A | | 12/1996 | Viegas et al. |
| 5,710,148 A | | 1/1998 | Sudo et al. |
| 5,728,405 A | | 3/1998 | McDonnell |
| 5,770,628 A | | 6/1998 | Cantoro |
| 5,861,955 A | | 1/1999 | Gordon |
| 5,871,772 A | | 2/1999 | Cantoro |
| 5,958,443 A | | 9/1999 | Viegas et al. |

FOREIGN PATENT DOCUMENTS

| | | |
|---|---|---|
| EP | 0 517 970 | 12/1992 |
| GB | 2 196 255 | 4/1988 |
| WO | WO 94/10976 | 5/1994 |
| WO | WO 95/13768 | 5/1995 |
| WO | WO 97/28787 | 8/1997 |
| WO | WO 98/08048 | 2/1998 |
| WO | WO 98/29069 | 7/1998 |
| WO | WO 98/37903 | 9/1998 |
| WO | WO 99/06023 | 2/1999 |
| WO | WO 99/51273 | 10/1999 |
| WO | WO 02/24116 | 3/2002 |

OTHER PUBLICATIONS

Pallikaris, et al., "*Laser In–Situ Keratomileusis*", Lasers in Surgery and Medicine, vol. 10; pp. 463–468; (1990).

Farah, et al., "*Laser In–Situ Keratomileusis: Literature Review of a Developing Technique*"; Journal of Cataract and Refractive Surgery, vol. 24; pp. 989–1006; (Jul. 1998).

Gimbel, et al., "*Indications, Results, and Complications of LASIK*", Current Opinion in Ophthalmology; vol. 9; pp. 3–8 (1998).

Carr, et al., "*Laser In–Situ Keratomileusis*", Ophthalmology Clinics of North America, vol. 10; pp. 533–542; No. 4; (Dec. 1997).

Hatsis, "*80% Balanced Salt Solution to Reduce Post–LASIK Flap Striae and Wrinkles*", Symposium on Cataract, IOL and Refractive Surgery, American Society of Cataract and Refractive Surgery, Apr. 10–14, 1999.

Wilson, "*LASIK Surgery*", AORN Journal, vol. 71, pp. 963–983; (2000).

\* cited by examiner

Primary Examiner—James O. Wilson
Assistant Examiner—Ganapathy Krishnan
(74) Attorney, Agent, or Firm—Gregg C. Brown

(57) ABSTRACT

Ocular lubricant solutions are described. The solutions are adapted to facilitate the formation of a corneal flap during LASIK surgery. The solutions contain one or more viscosity enhancing agents (e.g., chondroitin sulfate) in a substantially salt-free, ophthalmically acceptable vehicle. Methods of lubricating the cornea to facilitate flap formation are also described.

7 Claims, No Drawings

OPHTHALMIC LUBRICATING SOLUTION ADAPTED FOR USE IN LASIK SURGERY

This application claims priority from International Patent Application No. PCT/US01/44533 filed on Nov. 29, 2001, which claims priority from U.S. Provisional Application Ser. No. 60/257,304, filed on Dec. 20, 2000.

BACKGROUND OF THE INVENTION

The present invention is directed to the field of ophthalmic surgery. More specifically, the invention is directed to a lubricating solution that may be utilized during various ophthalmic procedures, but is particularly useful in facilitating the formation of a corneal flap during laser in situ keratomileusis ("LASIK").

LASIK surgery involves the use of a microkeratome to make an incision in the cornea transverse to the optical axis. This incision results in the formation of a corneal flap which is temporarily lifted and folded back so as to expose underlying tissue which is then sculpted or ablated with a laser so as to modify the curvature of the cornea and thereby correct the vision of the patient. For further background regarding LASIK surgery, particularly the formation of the corneal flap by means of a microkeratome, please refer to the following publications:

Pallikaris et al., *"Laser In-Situ Keratomileusis", Lasers in Surgery and Medicine*, volume 10, Pages 463–468 (1990);

Carr et al., *"Laser In-Situ Keratomileusis", Ophthalmology Clinics of North America* volume 10, pages 533–543 (1997);

Gimbel et al., *"Indications, Results, and Complications of LASIK", Current Opinion in Ophthalmology*, volume 9, pages 3–8 (1998);

Farah et al., *"Laser In-Situ Keratomileusis: Literature Review of a Developing Technique" Journal of Cataract and Refractive Surgery*, volume 24, pages 1059–1063 (1998); and Wilson, *"LASIK Surgery", AORN Journal*, volume 71, pages 963–983 (2000).

Although the LASIK surgical procedure has now been conducted on thousands of patients, certain aspects of the procedure occasionally give rise to complications. The formation of the corneal flap is one aspect of the overall LASIK procedure which can give rise to complications. Specifically, the formation of the corneal flap can result in epithelial abrasions or other damage due to the microkeratome blade, and the cut or incision by means of the microkeratome blade can sometimes be somewhat unpredictable. Moreover, in some patients, corneal haze or edema subsequent to surgery and flap wrinkles or curled flap edges have been attributed to problems in forming the corneal flap with the microkeratome. The failure of the flap to reseal following surgery is also a significant complication, because such failure creates a greater risk of infection and may adversely affect visual acuity.

In view of the foregoing, there is a need for products which will enhance the ability of surgeons to form the corneal flap without damaging the cornea or associated ophthalmic tissues. In particular, there is a need for products which: (1) help to minimize corneal epithelial abrasions; (2) facilitate smooth, consistent cuts; and (3) expedite post-operative visual acuity by facilitating formation of a flap that is not wrinkled, fits well upon replacement and seals readily following the LASIK procedure.

Various types of solutions are currently being applied to the cornea prior to use of the microkeratome to form the corneal flap in LASIK surgical procedures. However, none of these solutions has been designed to meet the needs of the ophthalmic surgeon in conjunction with LASIK surgery. Consequently, each of these solutions has one or more drawbacks. For example, some of the solutions provide at least minimal lubrication, but contain other ingredients (e.g., antimicrobial preservatives) which are potentially toxic to the cornea and therefore highly undesirable in conjunction with an invasive surgical procedure such as LASIK surgery. Thus, the solutions currently being utilized are, at best, less than ideal.

The prior solutions have also created a problem with respect to the surgical devices utilized in the LASIK procedure. Specifically, the balanced salt solutions and other electrolyte-containing solutions which have been used to lubricate the cornea prior to formation of the corneal flap with a microkeratome contain relatively high concentrations of sodium chloride and other salts. The microkeratome is a very delicate, precise surgical instrument that includes a small motor and a gear-driven blade. The effectiveness and accuracy of the microkeratome in forming the corneal flap is directly dependent on the motor and gears. It has been found that the electrolyte solutions can create a corrosion or gumming problem on the motor and/or gears of the microkeratome and thereby interfere with its performance. Thus, there is a need not only for a lubricant solution which enhances the ability of the surgeon to form the corneal flap, but also for a solution which does not have any negative effects on the performance of the microkeratome.

SUMMARY OF THE INVENTION

The present invention provides an improved lubricating solution for topical application to the cornea in conjunction with ophthalmic surgical procedures, particularly the formation of a corneal flap in conjunction with LASIK surgery.

The lubricating solution of the present invention is salt-free, and therefore does not create a risk of corrosion to the motor, gear system or other components of microkeratome devices.

The solutions of the present invention are also unpreserved, that is, the solutions do not contain antimicrobial preservatives (e.g., benzalkonium chloride). Such preservatives are potentially harmful to the cornea, particularly in patients undergoing LASIK surgery.

Finally, the solutions of the present invention contain a viscosity-enhancing agent to modify the lubricity or tackiness of the solution upon application to the cornea. The viscosity-enhancing agent facilitates formation of the corneal flap with less force and less potential damage to the tissues from either the microkeratome blade or the vacuum ring is utilized to hold the cornea in place during formation of the corneal flap.

DETAILED DESCRIPTION OF THE INVENTION

The lubricant solutions of the present invention are substantially salt-free. As utilized herein, the phrase "substantially salt-free" means that the solutions contain only incidental amounts of ionic salts such as sodium chloride or, preferably, do not contain any ionic salts.

Because ionic salts are largely absent from the solutions of the present invention, it is necessary to adjust the osmolality of the solutions with other types of materials. Various non-ionic osmolality-adjusting agents can be utilized for this purpose. Examples of such agents include various polyhydric alcohols, such as glycerol, mannitol, sorbitol, propylene glycol, and so on. The most preferred non-ionic osmolality adjusting agent is glycerol.

The above-described non-ionic osmolality adjusting agents will be utilized in an amount sufficient to render the solutions either isotonic, mildly hypotonic, or mildly hypertonic. The osmolality range for the solutions of the present invention will typically be about 200 to 400 milliosmoles per kilogram water ("mOsm/kg").

The lubricant solutions of the present invention are sterile and do not contain antimicrobial preservatives such as benzalkonium chloride. The solutions are therefore referred to herein as being "unpreserved".

In order to provide lubrication of the microkeratome, reduce corneal epithelial abrasions from the microkeratome blade, and produce smooth and consistent cuts with the microkeratome blade, the lubricant solutions of the present invention include a small amount of one or more viscosity-enhancing agents.

The viscosity-enhancing agent is preferably a polymeric material. Various pharmaceutically acceptable polymeric materials can be used for this purpose. The preferred polymeric materials include: chondroitin sulfate, sodium hyaluronate or other proteoglycans; cellulose derivatives, such as hydroxypropyl methylcellulose ("HPMC"), carboxy methylcellulose ("CMC"), and hydroxyethyl cellulose ("HEC"); collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); xanthan gum; gellan gums; alginate; chitosans; polyvinyl alcohol; carboxyvinyl polymers (e.g., carbomers such as the Carbopol™ brand polymers available from B. F. Goodrich); and various other viscous or viscoelastomeric substances, including but not limited to those described in U.S. Pat. No. 5,409,904 (Hecht, et al.), the entire contents of which are hereby incorporated by reference in the present specification.

The following patent publications may be referred to for further details concerning the above-listed viscosity-enhancing agents: U.S. Pat. No. 4,861,760 (gellan gums); U.S. Pat. No. 4,255,415 and WIPO Publication No. WO 94/10976 (polyvinyl alcohol); U.S. Pat. No. 4,271,143 (carboxyvinyl polymers); WIPO Publication No. WO 99/51273 (xanthan gum); and WIPO Publication No. WO 99/06023 (galactomannans). The entire contents of the foregoing references pertaining to the structures, chemical properties and physical properties of the respective viscosity enhancing agents described above are hereby incorporated in the present specification by reference.

The most preferred viscosity-enhancing agent is chondroitin sulfate. The use of chondroitin sulfate in an amount of 0.1 to 10 w/v % allows the above-stated objectives to be achieved. Moreover, the use of chondroitin sulfate is also advantageous in that it can serve not only as the viscosity-enhancing agent, but also as an osmolality-enhancing agent.

As indicated above, the viscosity-enhancing agent modifies the lubricity or tackiness of the lubricant solution so as to facilitate the formation of the corneal flap with less force applied to the microkeratome blade. The viscosity-enhancing agent also helps to prevent damage to ophthalmic tissue from the microkeratome blade or the vacuum ring that is applied to the cornea to hold it in place. The amount of polymeric material required in order to achieve these objectives is referred to herein as "an effective amount". The amount required will vary depending on the polymeric material or combination of materials selected in a given case and other considerations. However, the concentration of the polymeric material in the lubricant solutions of the present invention will generally be in the range of from about 0.1 to about 10 weight/volume percent ("w/v %"), and the viscosity of the solutions will generally be in the range of 1 to 50 centipoises ("cps"), preferably 3 to 30 cps.

The lubricant solutions of the present invention may be utilized in conjunction with various types of ophthalmic surgical procedures, but are particularly adapted for use in LASIK surgery. The solutions may be utilized to facilitate formation of the corneal flap by applying a few drops of the solution to the cornea immediately before the microkeratome is applied to the cornea.

Although the solutions of the present invention are primarily intended to be utilized during LASIK surgery to facilitate formation of the corneal flap, the lubricant properties of the solutions also makes the solutions quite useful for post-surgical application by the physician or patient. Patients who have LASIK surgery frequently report feelings of dryness, increased sensitivity or other minor irritations subsequent to the surgical procedure. The solutions of the present invention may be employed to alleviate or reduce these types of post-surgical symptoms.

The following examples are provided to further illustrate the lubricant solutions of the present invention.

EXAMPLE 1

| Ingredient | Amount (w/v %) |
|---|---|
| Chondroitin Sulfate | 0–10 |
| Glycerin | 1–3% (to adjust tonicity) |
| Hydrochloric acid/Sodium Hydroxide | qs to pH 6.5–8.5 |
| Water for Injection | qs to volume |

The solution is prepared by dissolving appropriate amount of glycerin in water for injection at about 20° C. to adjust the osmolality of the solution to the desired level. Chondroitin sulfate is then added to the solution to make the concentration of chondroitin sulfate in the range of 0 to 10% weight by volume. The pH of the solution is adjusted to the range of 6.5 to 8.5 by adding 1N HCl or 1N NaOH. Additional water for injection is then added to bring the solution to its final volume.

EXAMPLE 2

| Ingredient | Amount (w/v %) |
|---|---|
| Hydroxypropyl Methylcellulose (HPMC) | 0–1 |
| Glycerin | 1–3% |
| Hydrochloric acid/Sodium Hydroxide | qs to pH 6.5–8.5 |
| Water for Injection | qs to volume |

The solution is prepared by dissolving appropriate amount of glycerin in water for injection at about 20° C. to adjust the osmolality of the solution to the desired level. The solution is heated till it is about to boil. Hydroxypropyl methylcellulose is then added to the heated solution under rigorous stirring to make the concentration of HPMC in the range of 0 to 1% weight by volume. The solution is removed from heat and let cool to room temperature under continuous stirring. The solution is then stored under refrigeration overnight to facilitate complete hydration of HPMC. The next day the solution is brought to room temperature and the pH of the solution is adjusted to the range of 6.5 to 8.5 by adding 1N HCl or 1N NaOH. Additional water for injection is then added to bring the solution to its final volume.

We claim:

1. A method of facilitating the formation of a corneal flap in LASIK surgery by means of a microkeratome and reducing the risk of abrasions to corneal tissue during the formation of said flap, which comprises applying an ocular lubricant solution to the corneal surface of an eye immediately before the microkeratome is applied to the eye, said solution comprising a viscosity-enhancing agent in an amount effective to enhance the viscosity of the solution, and an ophthalmically acceptable vehicle for said viscosity-enhancing agent, wherein the solution is sterile, unpreserved and substantially salt free.

2. A method according to claim 1, wherein the lubricant solution has a viscosity of 1 to 50 cps.

3. A method according to claim 1, wherein the viscosity-enhancing agent is selected from the group consisting of: proteoglycans; cellulose derivatives; collagen or modified collagen; galactomannans; xanthan gum; gellan gum; alginate; chitosans; polyvinyl alcohol; and carboxyvinyl polymers.

4. A method according to claim 3, wherein the viscosity-enhancing agent comprises a proteoglycan.

5. A method according to claim 4, wherein the proteoglycan is selected from the group consisting of chondroitin sulfate and sodium hyaluronate.

6. A method according to claim 5, wherein the viscosity-enhancing agent comprises chondroitin sulfate.

7. A method according to claim 1, wherein the lubricant solution has a viscosity of 3 to 30 cps.

* * * * *